US012102907B2

(12) United States Patent
Wachi et al.

(10) Patent No.: US 12,102,907 B2
(45) Date of Patent: Oct. 1, 2024

(54) GAME DEVICE AND COMPUTER-READABLE RECORDING MEDIUM

(71) Applicant: TANITA CORPORATION, Tokyo (JP)

(72) Inventors: Yuto Wachi, Tokyo (JP); Mana Akao, Tokyo (JP)

(73) Assignee: TANITA CORPORATION, Tokyo (JP)

( * ) Notice: Subject to any disclaimer, the term of this patent is extended or adjusted under 35 U.S.C. 154(b) by 142 days.

(21) Appl. No.: 17/808,350

(22) Filed: Jun. 23, 2022

(65) Prior Publication Data

US 2022/0314111 A1 Oct. 6, 2022

Related U.S. Application Data

(63) Continuation of application No. PCT/JP2020/047675, filed on Dec. 21, 2020.

(30) Foreign Application Priority Data

Dec. 23, 2019 (JP) ................................. 2019-231842

(51) Int. Cl.
  *A63F 13/23* (2014.01)
  *A61B 5/0537* (2021.01)
  *A63F 13/21* (2014.01)
  *A63F 13/79* (2014.01)

(52) U.S. Cl.
  CPC ............ *A63F 13/23* (2014.09); *A61B 5/0537* (2013.01); *A63F 13/21* (2014.09); *A63F 13/79* (2014.09); *A63F 2300/10* (2013.01)

(58) Field of Classification Search
  None
  See application file for complete search history.

(56) References Cited

U.S. PATENT DOCUMENTS

2009/0029769 A1*  1/2009  Muller ................... A63F 13/58
                                                  463/31
2014/0025346 A1*  1/2014  Uchiyama ............ A61B 5/1072
                                                  703/1

(Continued)

FOREIGN PATENT DOCUMENTS

EP      2 394 718 A2    12/2011
JP      H10-24172 A      1/1998

(Continued)

OTHER PUBLICATIONS

International Search Report issued in PCT/JP2020/047675; mailed Jan. 26, 2021.

*Primary Examiner* — Jason T Yen
(74) *Attorney, Agent, or Firm* — Studebaker & Brackett PC

(57) ABSTRACT

A game device includes a storage unit and a control unit configured to execute a game program. The control unit acquires biological information indicating physical feature of a user operating the game device, computes a biological parameter of the user based on the biological information, and stores the biological parameter in the storage unit. The control unit then computes, in accordance with the biological parameter stored in the storage unit, a property parameter that determines a property of a character generated by the game program.

20 Claims, 11 Drawing Sheets

(56) References Cited

U.S. PATENT DOCUMENTS

| | | | | |
|---|---|---|---|---|
| 2016/0086500 A1* | 3/2016 | Kaleal, III | ............... | A61B 5/45 |
| | | | | 434/257 |
| 2017/0061668 A1* | 3/2017 | Takafuji | .................. | A63F 13/56 |
| 2018/0214767 A1* | 8/2018 | Oh | ........................... | G06T 13/20 |
| 2018/0280804 A1* | 10/2018 | Minagawa | ............ | A63F 13/577 |
| 2019/0030423 A1 | 1/2019 | Onozawa et al. | | |
| 2020/0118349 A1* | 4/2020 | Amimoto | ................ | A63F 13/63 |

FOREIGN PATENT DOCUMENTS

| | | | | |
|---|---|---|---|---|
| JP | 2000-126464 A | 5/2000 | | |
| JP | 2002-263362 | * 9/2002 | ............ | A63F 13/00 |
| JP | 2002-263362 A | 9/2002 | | |
| JP | 5108156 B1 | 12/2012 | | |
| JP | 2014-018444 A | 2/2014 | | |
| JP | 2016-067537 A | 5/2016 | | |
| JP | 6544869 B2 | 7/2019 | | |
| WO | 2018/216602 A1 | 11/2018 | | |

* cited by examiner

| BIOLOGICAL PARAMETER | PROPERTY PARAMETER |
|---|---|
| CIRCUMFERENCE | BODY WIDTH |
| MUSCLE MASS, BODY FAT PERCENTAGE | ATTACKING POWER |

FIG.5

GAME DEVICE AND COMPUTER-READABLE RECORDING MEDIUM

TECHNICAL FIELD

The present invention relates to a game device and a computer-readable recording medium.

BACKGROUND ART

JP6544869B discloses an information processing device in which a user of a game operates an object in the game in accordance with a posture of a controller including a gyroscope sensor. In addition, JP1998-24172A discloses a game machine in which a shape of an object in the game, which is a control target, is changed on the basis of a bio-signal.

However, in the information processing device disclosed in JP6544869B, for example, when users with different physical functions from each other perform operations such that the posture of the controller becomes the same, even if the physical functions of the respective users are different, no difference is caused between the motions of the objects in the game. As described above, because the user's own features are not reflected to the object in the game, immersive feeling of the user for the game is deteriorated.

In addition, with the game machine disclosed in JP1998-24172A, the shape of the object in the game is changed with biological information of the user acquired during the operation of the game. Thus, for example, as processing for the changes of the shape of the object in the game becomes complex, time required to reflect the processing for the changes is increased. As described above, the immersive feeling of the user for the game is also deteriorated due to a loss of a real-time nature of the game.

As described above, factors for deteriorating the immersive feeling of the user for the game include the fact that the user's own features are not reflected to the object in the game and that the real-time nature of the game is lost, and it had been difficult to achieve the both at the same time.

In light of the circumstances described above, an object of the present invention is to provide a game device and a computer-readable recording medium that provides an immersive feeling to a user.

SUMMARY OF INVENTION

According to one aspect of the present invention, provided is a game device including a storage unit and a control unit configured to execute a game program, wherein the control unit is configured to: acquire biological information indicating physical feature of a user; compute a biological parameter of the user based on the biological information; store the biological parameter of the user in the storage unit; and compute a property parameter in accordance with the biological parameter stored in the storage unit, the property parameter determining a property of a character generated by the game program.

According to one aspect of the present invention, at least any one of physical function and external appearance of the user is reflected to the character in the game without interrupting a progression of the game. Thus, it is possible to provide the game device and the computer-readable recording medium that provides the immersive feeling to the user.

BRIEF DESCRIPTION OF DRAWINGS

FIG. 5 is a diagram showing one example of an associating relationship between a biological parameter and a property parameter.

DESCRIPTION OF EMBODIMENTS

A game system according to respective embodiments of the present invention will be described below with reference to the drawings.

First Embodiment

[System Configuration]

Figure 1:
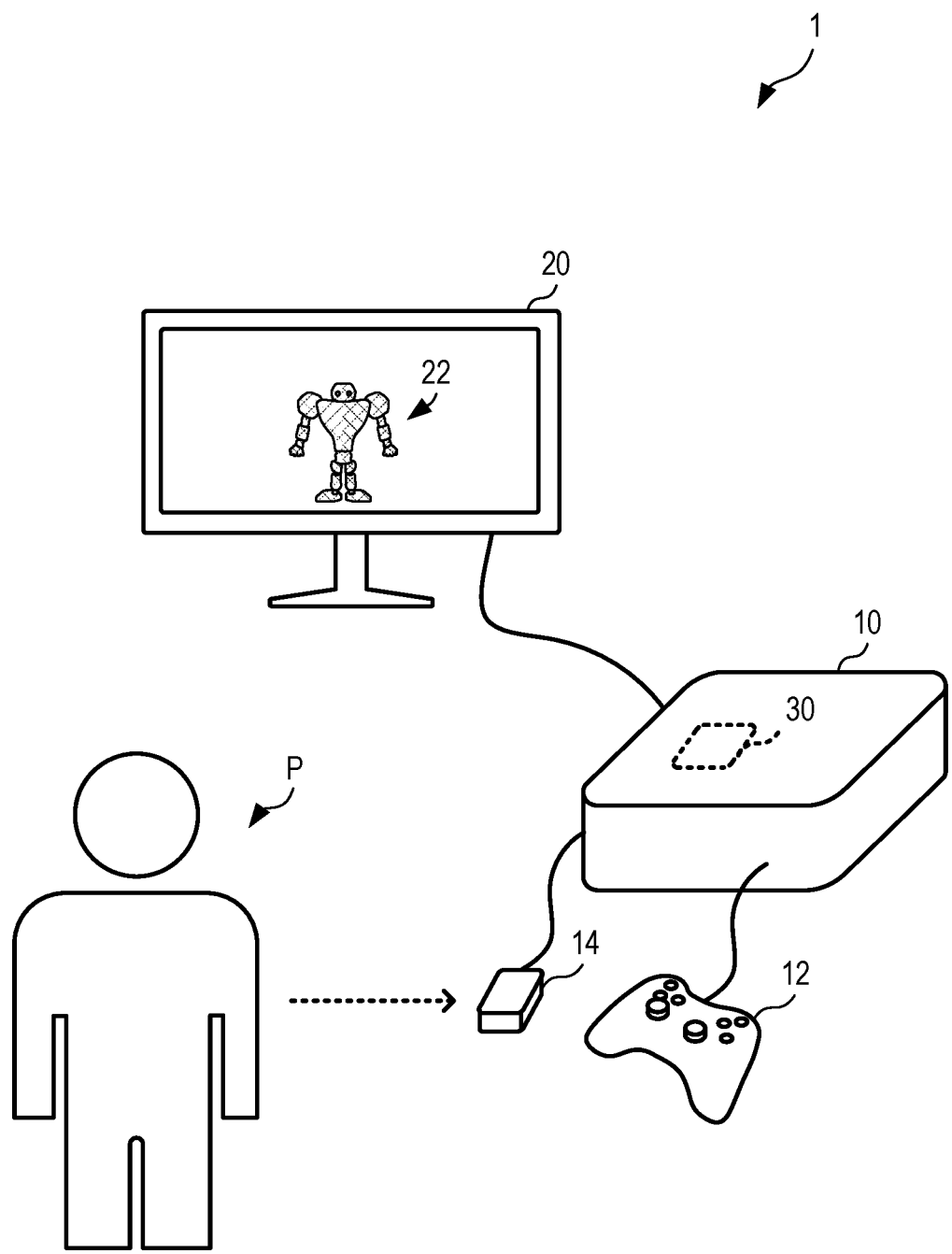
FIG. 1 is a diagram showing one example of a schematic configuration of a game system in a first embodiment.

A game system 1 to which a game device 10 according to a first embodiment is applied will be described first with reference to FIG. 1. FIG. 1 is a diagram showing a schematic configuration of the game system 1.

The game system 1 in this embodiment is a system that is capable of reflecting a feature of a user P of a game to a character appears in an electronic game. The feature of the user P in this context refers to, for example, at least any one of the physical function of the user P and an external appearance (body shape) of the user P. In this embodiment, the feature of the user P will be described by referring it mainly as "biological information", "biological parameter", "the physical function", or "the external appearance".

The game system 1 includes the game device 10 and a display device 20. In addition, the game device 10 has a controller 12 and a bio-sensor 14.

The game device 10 is a device that executes a game program stored in a removable storage medium 30. The game program is a game that is progressed as the user P operates the character displayed on the display device 20. The game program stored in the storage medium 30 is a program that generates, for example, the electronic game such as a so-called action game, role playing game, shooting game, sport game, or the like, and the present invention is not limited thereto.

As the game device 10 executes the game program stored in the storage medium 30, the display device 20 displays a character image 22 that is an image of the character generated by the game device 10.

The controller 12 is an operating unit that allows the user P to operate the character image 22 displayed on the display device 20. The controller 12 sends a control signal in response to operation of buttons by the user P to the game device 10 via a wireless transmission or a wired transmission. As one example, the controller 12 in this embodiment is connected to the game device 10 via a wire. The game device 10 controls movement of the character image 22 on a screen of the display device 20 in response to the control signal received from the controller 12.

The bio-sensor 14 acquires biological information of the user P obtained by converting a physical feature of the user P to a numerical value by being brought into contact with the user P, for example, by being held by the user P, and the bio-sensor 14 sends the biological information to the game device 10 via the wireless transmission or the wired transmission. As one example, the bio-sensor 14 in this embodiment is connected to the game device 10 via the wire.

The biological information of the user P that is sent from the bio-sensor 14 is used to determine a property of the character, which will be described later, in the game device 10. As described in detail below, the game device 10 determines at least any one of the external appearance of the character and the physical function of the character as a property of the character by using a biological parameter computed from the biological information of the user P.

The display device 20 is formed of, for example, a liquid crystal display and is a display unit that displays an image in response to an image signal from the game device 10. For example, as the display device 20 receives the image signal of the character image 22 from the game device 10, the display device 20 displays the character image 22.

The storage medium 30 is formed of, for example, a CD-ROM, or SD Card®. The storage medium 30 in this embodiment stores the game program that is readable by the game device 10.

With the configuration described above, while the game program is executed by the game device 10, the feature of the user P (the biological parameter) computed by using the biological information unique to the user P is reflected to the character defined by the game program by the game device 10. The user P can then play the game by moving the character image 22 that reflects his/her own feature.

Definition of Terms

Terms used in this embodiment will be described. In this embodiment, the biological parameter refers to a parameter that indicates at least any one of the physical function and the external appearance of the user P. Types of the biological parameter include, for example, muscle mass, and body fat percentage. In addition, a value of the biological parameter is obtained from the biological information obtained by converting the feature of the user P to the numerical value.

In this embodiment, a property parameter refers to a parameter that indicates at least any one of the physical function and the external appearance of the character in a virtual space. Types of the property parameter include, for example, jumping power and attacking power as the physical function of the character. In addition, the value of the property parameter is obtained from the value of the biological parameter as described below in more detail.

[Functional Configuration]

Figure 2:
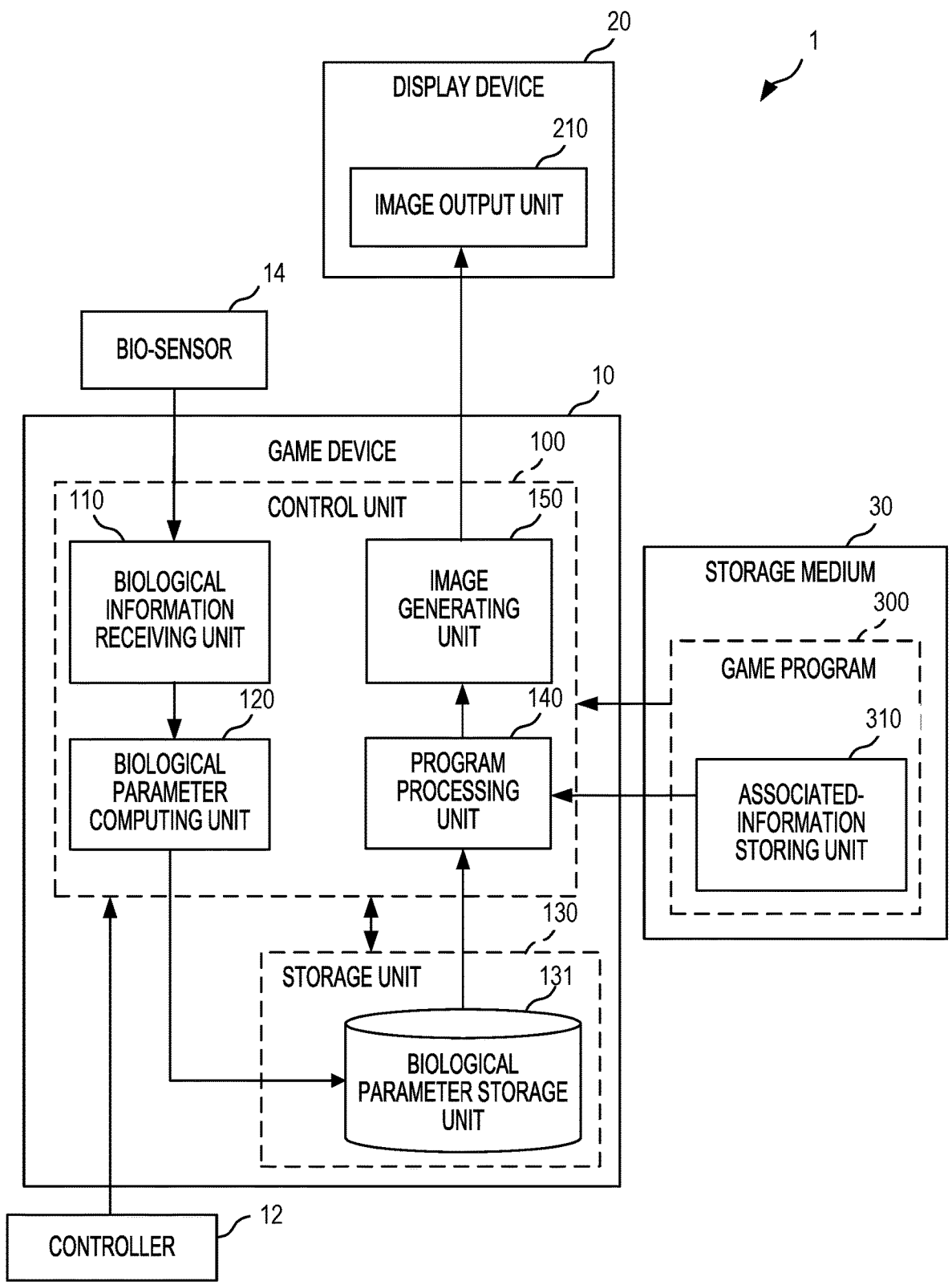
FIG. 2 is a diagram showing one example of a functional configuration of the game system in the present embodiment.

Next, a functional configuration of the game system 1 in this embodiment will be described. FIG. 2 is a diagram showing one example of a functional configuration of the game system 1 of this embodiment.

The bio-sensor 14 will be described first. The bio-sensor 14 is provided with at least one sensor capable of detecting the feature of the user P as the biological information. The bio-sensor 14 in this embodiment is provided with, as one example, a pair of electrodes that detect biological impedance as the biological information of the user P. As the biological information, the bio-sensor 14 may be configured so as to be able to detect at least one of body image data, body temperature distribution data, and elasticity index of skin of the user P instead of or in addition to the biological impedance.

Once the bio-sensor 14 in this embodiment is held by the user P, an electrical power is applied to a pair of electrodes. By doing so, the bio-sensor 14 detects the biological impedance of the user P. The biological impedance is detected as a resistance value in ohms as a unit in general. The bio-sensor 14 sends the numerical value of the biological impedance of the user P detected to the game device 10.

In addition, the bio-sensor 14 may be provided with an input unit (not shown). In this case, the bio-sensor 14 may be formed so as to receive input of numerical value such as a body height, etc. of the user P via the input unit. Once the bio-sensor 14 detects the input of the biological information such as the body height, etc. of the user P, the bio-sensor 14 sends the numerical value to the game device 10. The input unit may receive input of other biological information such as body weight, etc. instead of or in addition to the body height.

In this embodiment, for ease of understanding, description will be given by assuming a case in which the biological impedance and the body height are used as the biological information.

Next, the game device 10 connected to the bio-sensor 14 will be described. The game device 10 is provided with a control unit 100 and a storage unit 130.

The control unit 100 performs control of entire game device 10. The control unit 100 is provided with a biological information receiving unit 110, a biological parameter computing unit 120, a program processing unit 140, and an image generating unit 150.

In addition, the control unit 100 is formed of a central processing unit, an input/output interface, and a bus that connects these components with each other. The control unit 100 controls respective parts of the game device 10 via the input/output interface by reading out a control program stored in the storage unit 130 to cause the central processing unit to execute it.

The biological information receiving unit 110 receives the biological information of the user P that has been converted into the numerical value by the bio-sensor 14. In this embodiment, the biological information receiving unit 110 receives the biological impedance of the user P and the body height of the user P and sends the numerical values thereof to the biological parameter computing unit 120.

The biological parameter computing unit 120 converts a part or all of the biological information, which has been converted into the numerical values, received from the biological information receiving unit 110 to the biological parameter. Specifically, the biological parameter computing unit 120 computes the body fat percentage and the muscle mass as the biological parameter of the user P from the biological impedance of the user P and the body height of the user P.

The storage unit 130 is formed of at least any one of, for example, a non-volatile memory (a read only memory) and a volatile memory (a random access memory). The storage unit 130 stores the control program that controls the operation of the game device 10. In other words, the storage unit 130 is a non-transitory storage medium that stores a program that realizes the functions of this embodiment.

In addition, the storage unit 130 includes a biological parameter storage unit 131 in a part of a storage area. The biological parameter storage unit 131 stores the biological parameter computed by the biological parameter computing unit 120. In this embodiment, the body fat percentage and the muscle mass as the biological parameter are stored so as to be associated with identification information of the user P.

The program processing unit 140 computes the property parameter by using the biological parameter that is read out from the biological parameter storage unit 131. The program processing unit 140 then sends the property parameter to the image generating unit 150. In more detail, the program processing unit 140 receives a program for computing the property parameter from an associated-information storing unit 310, which will be described later, and computes the property parameter by using this program. The property parameter in this context is a unique parameter indicating the property of the character that is set in advance for each character that appears in the game by executing a game program 300. As described below in more detail, because the property parameter is associated with the biological parameter, the value of the property parameter is changed in accordance with the value of the biological information of the user P.

The image generating unit 150 generates the character image 22 that is the image of the character. For example, the image generating unit 150 in this embodiment may generate the character image 22 by selecting a specific image from images of a plurality of characters stored in the storage unit 130 in advance. The generating processing performed by the character image 22 will be described below in more detail. The image generating unit 150 stores the image signal of the thus-generated character image 22 in one region of the storage unit 130.

In addition, the image generating unit 150 sends the image signal of the thus-generated character image 22 to an image output unit 210 of the display device 20. The image output unit 210 uses the image signal of the character image 22 to outputs the image of the character image 22 on the screen of the display device 20.

Next, the storage medium 30 connected to the game device 10 will be described.

The storage medium 30 stores the game program 300 that is to be played by the user P. The game program 300 in this embodiment is a program that is classified as a so-called action game. In addition, the game program 300 is a program that moves the character in the virtual space in response to the operation of the controller 12 by the user P, thereby causing the processing to proceed in response to the movement of the character. The property of the character, in other words, the physical function of the character in the virtual space that is generated by the game program 300 in this embodiment will be described below in more detail.

The storage medium 30, which stores the game program 300 in this embodiment, includes the associated-information storing unit 310.

The associated-information storing unit 310 has information associating the biological parameter with the property parameter. The associated-information storing unit 310 in this embodiment has an arithmetic expression for converting the biological parameter of the user P to the property parameter of the character. The property parameter is the unique parameter that is set for each character generated by the game program 300.

Specifically, one example of the property parameter that reflects the biological information of the user P includes the attacking power indicating a level of power of the character in the virtual space. In this case, the associated-information storing unit 310 in this embodiment has the arithmetic expression for converting the fat mass and the muscle mass of the user P to the attacking power as the property parameter of the character. The associated-information storing unit 310 sends the arithmetic expression for converting the biological parameter to the property parameter to the program processing unit 140 of the game device 10 in response to a controlling signal from the control unit 100.

Instead of or in addition to the arithmetic expression, the associated-information storing unit 310 may have association information that associates the biological parameter with the property parameter in other format such as a table format.

As described above, in the game system 1 of this embodiment, the biological parameter obtained by converting the physical feature of the user P to the numerical value is computed. Then, as the game program 300 included in the storage medium 30 is executed, the property parameter that determines the property of the character is computed from the biological parameter.

The functions of respective units forming the game device 10 in this embodiment shown in FIG. 2 may be realized by either of a hardware or a software. For example, in a case in which the functions of the respective units are realized by the software, the respective functions included in the control unit 100 are stored in the storage unit 130 in advance as programs.

[Character Generating Processing]

Figure 3:
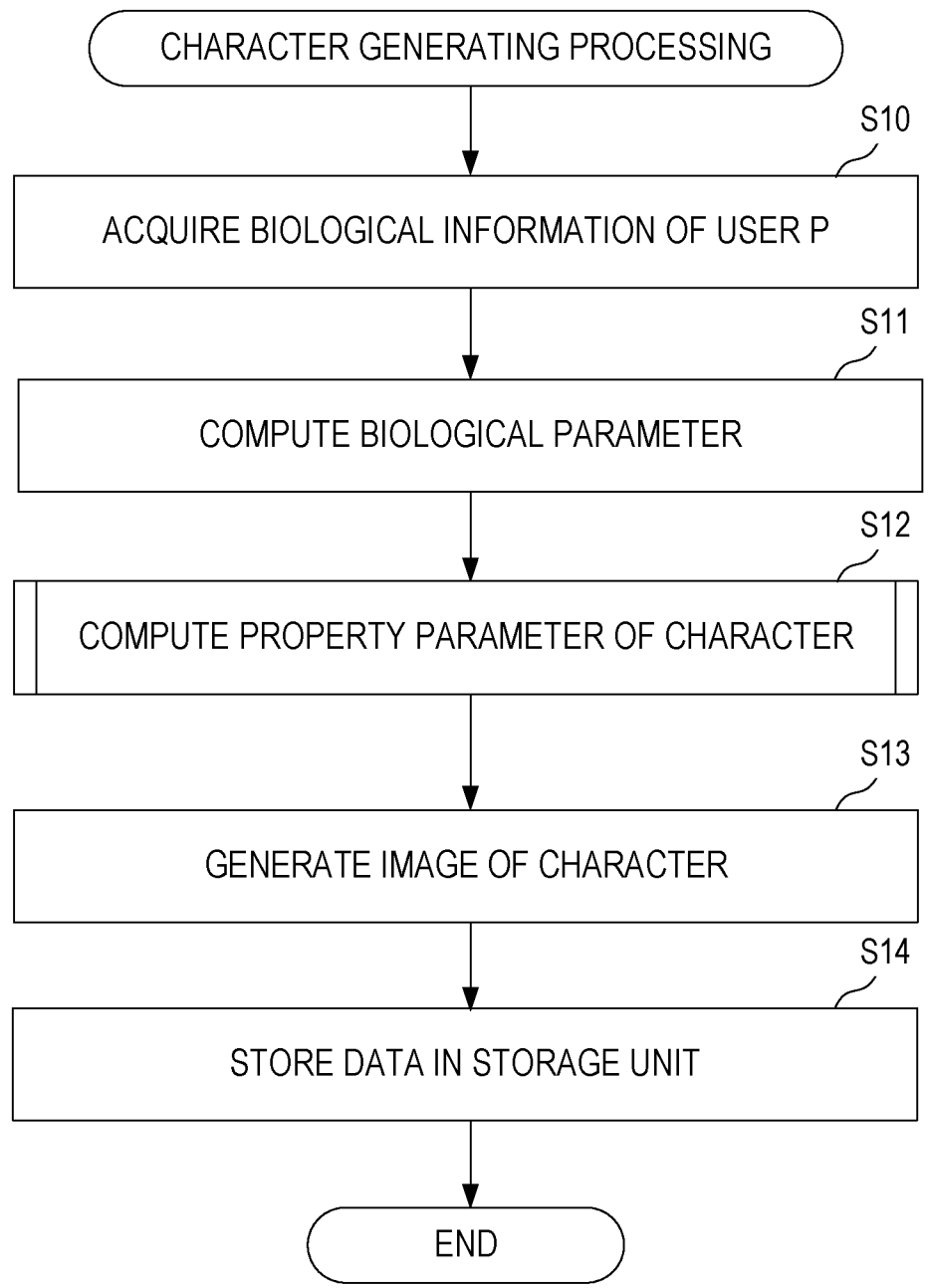
FIG. 3 is a flowchart showing one example of a character generating processing in the present embodiment.

Next, a character generating processing executed by the game device 10 in the game system 1 including the above-described functional configuration will be described. FIG. 3 is a flowchart showing one example of the character generating processing.

In the character generating processing in this embodiment, the character is generated in association with the property parameter that reflects the feature of the user P.

In step S10, the control unit 100 receives the biological information obtained by converting the feature of the user P to the numerical value by the biological information receiving unit 110. After the control unit 100 receives the biological information, the processing proceeds to step S11.

In step S11, the control unit 100 computes the biological parameter by the biological parameter computing unit 120. After the control unit 100 computes the biological parameter and the biological parameter is stored in the biological parameter storage unit 131, the processing proceeds to step S12.

The processings of steps S10 to S11 described above are preferably be executed before the user P starts playing the game, specifically, before the control unit 100 reads in the game program 300 stored in the storage medium 30. For example, the processing of steps S10 to S11 may be executed a few days or other predetermined hours before the game is to be played. Alternatively, the processing of steps S10 and S11 may be executed while the game device 10 is reading in the game program 300, or during other standby time such as a processing time for a scene change of the virtual space.

In other words, in order to suppress the delay of progression of the game, the processings of steps S10 to S11 is preferably be executed before the property of the character is determined at the latest, in other words, at an arbitrary timing before the property parameter is set.

In step S12, after the game program 300 read out from the storage medium 30 is executed, the control unit 100 computes the property parameter representing the physical function of the character that is to be generated in the game program 300. The property parameter is determined by executing a property-parameter generating processing, which will be described below. After the control unit 100 computes the property parameter, the processing proceeds to step S13.

In step S13, the control unit 100 generates the character image 22 that is the image of the character using the property parameter. Step S13 corresponds to an image generating step. After the control unit 100 generates the character image 22, the processing proceeds to step S14.

In step S14, the control unit 100 causes the storage unit 130 to store at least any one of the property parameter and the character image 22.

[Property-Parameter Generating Processing]

Figure 4:
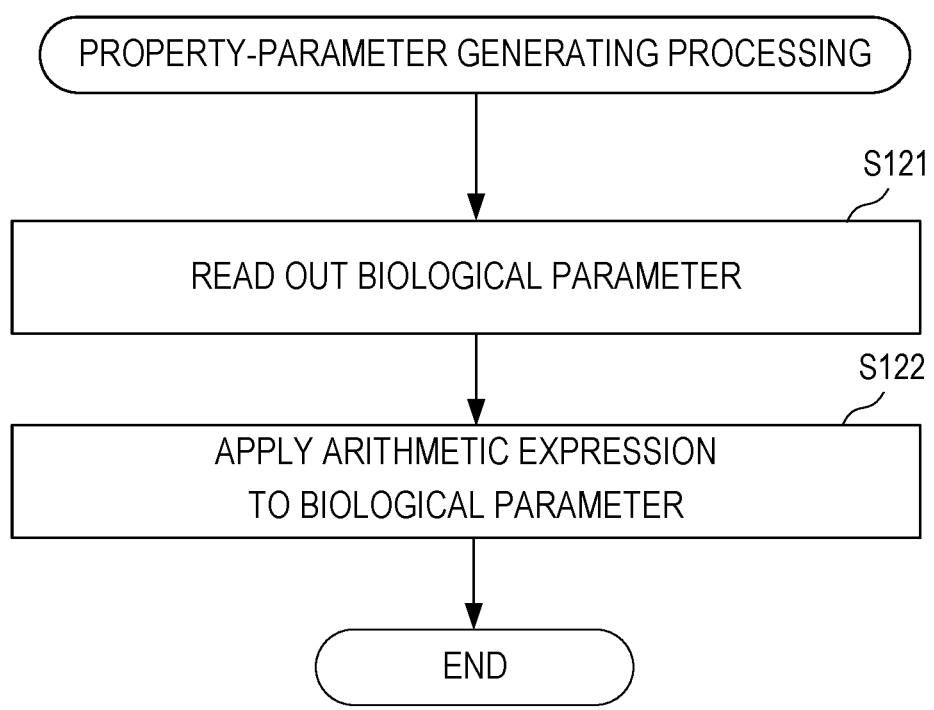
FIG. 4 is a flowchart showing one example of a property-parameter generating processing generated by a game program to which the present embodiment is applied.

In the above, the property-parameter generating processing included in the above-described character generating processing will be described. FIG. 4 is a flowchart showing one example of the property-parameter generating processing in this embodiment.

The property-parameter generating processing is executed by the control unit 100 as a subroutine of step S12 of the above-described character generating processing.

In step S121, the control unit 100 reads out the biological parameter of the user P from the biological parameter storage unit 131 and sends the biological parameter to the program processing unit 140. After the control unit 100 sends the biological parameter, the processing proceeds to step S122.

In step S122, the control unit 100 reads out the arithmetic expression for converting the biological parameter to the property parameter from the associated-information storing unit 310, and this is received by the program processing unit 140. The control unit 100 then computes the property parameter by applying the biological parameter to the arithmetic expression.

In the above, an associating relationship between the biological parameter and the property parameter will be described. FIG. 5 is a diagram showing one example of the associating relationship between the biological parameter and the property parameter.

In FIG. 5, the circumference of the user P is shown as the biological parameter. The circumference in this context includes a numerical value indicating a width of the body of the user P such as, for example, an abdominal circumference, a chest circumference, the circumference around shoulders, the circumference of arms or legs, and so forth. In the computation of the circumference of the user P, the fat mass and BMI, which can be calculated from values of the biological impedance and the body height for example, are used. Any known method may be used for the computation of the circumference of the user P.

The circumference as the biological parameter of the user P is associated with the body width of the character as the property parameter in the virtual space. Alternatively, the body width of the character can also be computed by using the arithmetic expression such as the following equation (1).

$$\text{Body Width of Character} = A \times \text{Circumference} + C \quad (1)$$

Coefficient A in the above equation (1) is a constant for weighting each biological parameter, and coefficient C is a constant for mainly normalizing the body width of the character into a specific numerical value range.

The body width of the character may be obtained by combining the biological parameter, such as the body fat percentage of the user P, etc., in addition to the circumference of the user P. For example, the body width of the character may be calculated by using the arithmetic expression such as the following equation (2), instead of the above equation (1).

$$\text{Body Width of Character} = A1 \times \text{Circumference} + B \times \text{Body Fat Percentage} + C1 \quad (2)$$

Respective coefficients A1 and B in the above equation (2) are constants for weighting the respective biological parameters. They may each be set independently by taking a degree of contribution to the body width of the character into consideration, and in order to be able to uniformly treat the numerical values of two biological parameters, the numerical values may be set such that various differences relative to the average value (standard) for every biological parameter are compensated. Coefficient C1 plays the similar role as C in the above equation (1).

For example, the control unit 100 determines presence/absence of a collider by using the body width of the character. The collider refers to a contact between the character in the virtual space and other object in a case in which a physical law is to be simulated by the game program 300.

The above-described collider will be described in detail by assuming, for example, a case in which the character moves so as to pass through between two poles in the virtual space realized by the game program 300. If the body width of the character associated with the circumference of the user P is larger than a distance between the two poles, the character comes to contact with the pole and cannot pass therethrough. In contrary, if the body width of the character associated with the circumference of the user P is smaller than the distance between the two poles, the character can pass through without coming into contact with the pole. As described above, the control unit 100 determines the presence/absence of the collider of the character with the other object by determining a size relationship between the distance between the two poles and the body width of the character.

In other words, when the control unit 100 determines the presence/absence of the collider in the virtual space realized by the game program 300, the control unit 100 uses the body width of the character as the threshold value for the determination. The body width as the property parameter in this embodiment may be associated by, for example, converting the circumference as the biological parameter of the user P to a numerical value suitable for the virtual space.

In addition, as another example shown in FIG. 5, a case in which the muscle mass and the body fat percentage as the biological parameter of the user P are associated with the attacking power indicating the level of the power of the character in the virtual space will be described. In this case, for example, an integrated value of the muscle mass and the body fat percentage as the biological parameter may be associated with the numerical value of the attacking power as the property parameter of the character.

Alternatively, the attacking power of the character may be computed by using the arithmetic expression expressed by the following equation (3).

$$\text{Attacking Power of Character} = D \times \text{Muscle Mass} + E \times \text{Body Fat Percentage} + F \quad (3)$$

Respective coefficients D and E in the above equation (3) are constants for weighting the respective biological parameters, and coefficient F is a constant for mainly normalizing the attacking power into a specific numerical value range. The coefficients D to F may each be set independently by taking contribution to the attacking power of the character, and in order to be able to uniformly treat the numerical values of two biological parameters, the numerical values may be set such that various differences relative to the average value for every biological parameter are compensated.

The attacking power of the character may not be associated with both of the muscle mass and the body fat percentage of the user P, but may be associated with at least any one of the biological parameters including the muscle mass, body fat, and the body weight.

For example, the attacking power of the character may be calculated by using the arithmetic expression such as the following equation (4), instead of the above equation (3).

$$\text{Attacking Power of Character} = D1 \times \text{Muscle Mass} + F1 \quad (4)$$

Similarly to the coefficients D and F in the above equation (3), respective coefficients D1 and F1 in the above equation (4) are set by taking the degree of contribution to and the normalization of the attacking power into consideration. By using the biological parameter with higher degree of contribution to the attacking power as in the above equation (4), it becomes possible to reflect the physical feature of the user P to the attacking power of the character with a simple processing.

Furthermore, at least one of the muscle mass and the body weight as the biological parameter of the user P may be associated with the jumping power of the character in the virtual space. Alternatively, the jumping power of the character may be obtained by using the arithmetic expression such as following equation (5) or (6).

$$\text{Jumping Power of Character} = G \times \text{Muscle Mass} + H \times \text{Body Weight} + I \quad (5)$$

$$\text{Jumping Power of Character} = G1 \times \text{Muscle Mass} + I1 \quad (6)$$

Respective coefficients G, G1, H, I, and I1 in the above-described equations (5) and (6) are set by taking the degree of contribution to and the normalization of the jumping power into consideration. For example, when the coefficient D or D1 in the equation (3) or (4) is set as a positive constant, the coefficients G and G1 may each be set as a negative constant such that the attacking power of the character and the jumping power are in a conflicting relationship.

For the associating relationship between the biological parameter and the property parameter, the association is not limited to a simple integration as described above, and the association may also be achieved by division, subtraction, or combinations thereof, and other computations. In other words, how and how much the biological parameter is associated with the property parameter is appropriately set.

As described above, In the property-parameter generating processing in this embodiment, the property parameter is associated with at least any one of the circumference, the muscle mass, and the body fat of the user P as the biological parameter indicating the feature of the user P.

In addition, the biological parameter can be set as an indicator indicating the physical function, in other words, the health status of the user P. For example, as the health status of the user P with a low health status is improved, the numerical value of the biological parameter may have a tendency to approach the standard value, and in addition, the numerical value of the property parameter of the character in the virtual space may also have a tendency to approach the standard value. In this context, the improvement of the health status means approach of the numerical value of the biological parameter to the numerical value indicating a good health status of the user P, such as approach of the numerical value of the biological parameter to the numerical value falling in a so-called normal range, improvement of the numerical value indicating a motor function among the biological parameter, or the like.

Of course, the associating relationship between the type of the biological parameter and the type of the property parameter is not limited to the associating relationship disclosed in this embodiment.

According to the above-described embodiment, following operations and effects are afforded.

The game device in this embodiment is the game device 10 that executes the game program 300 and is provided with the control unit 100 configured to control the game program 300 and the storage unit 130. The control unit 100 is configured to: acquire the biological information indicating the physical feature of the user P; compute the biological parameter of the user P on the basis of the biological information; and store the biological parameter in the storage unit 130. The control unit 100 then computes, in accordance with the biological parameter stored in the storage unit 130, the property parameter that determines the property of the character generated by the game program 300.

In addition, the game device 10 in this embodiment is a computer provided with the storage unit 130 and the control unit 100 that executes the game program 300. In a non-transitory computer-readable recording medium, a program that causes its computer to execute an acquisition step, a biological parameter computing step, a storing step, and a property-parameter computing step is recorded. In this embodiment, the acquisition step corresponds to step S10 in which the biological information indicating the physical feature of the user P is acquired, and the biological parameter computing step corresponds to step S11 in which the biological parameter of the user P is computed on the basis of the biological information of the user P. The storing step is a step in which the biological parameter of the user P is stored in the storage unit 130, and the property-parameter computing step corresponds to step S12 in which the property parameter that determines the property of the character generated by the game program 300 is computed in accordance with the biological parameter stored in the storage unit 130.

With the configuration described above, the biological information indicating the feature of the user P is reflected to the property of the character that appears by the execution of the game program 300. In this embodiment, because the physical function of the user P is reflected to the property of the character, in a case in which the physical function of the user P, for example, a quickness, stamina, or the like, is lowered, the physical function of the character in the virtual space is lowered.

As described above, in the game device 10, because the physical feature including the physical function of the user P is reflected to the character, the user P tends to be emotionally involved in the character, and it is possible to increase the immersive feeling of the user P to the game. Specifically, in the game device 10, by controlling the movement of the character displayed on the display device 20 in response to the control signal from the controller 12, it becomes easier for the user P to synchronize with the movement of the character in the virtual space, and the user P tends to have an affinity to the character. Therefore, it is possible to achieve the technical object in that continuous interaction between a human and a machine is facilitated.

In addition, the property parameter of the character is automatically set to the numerical value corresponding to the physical feature of the user P only by inputting the biological information of the user P himself/herself to the game device 10. By doing so, because the bothersome operational input by the user P is omitted compared with a case in which an operational input for setting the property of the character is performed by the user P while considering his/her own physical feature, it is possible to suitably reflect the physical feature of the user P to the character by the simple processing. In other words, even while the bothersome operational input by the user P is omitted, it is possible to suitably reflect the physical feature of the user P to the character. In other words, it is possible to solve two conflicting technical demands at the same time.

Furthermore, because the biological parameter is stored in the storage unit 130 by the game device 10, it is possible to compute and store the biological parameter before the user P plays the game. Alternatively, the game device 10 can also compute and store the biological parameter during a standby time while the user P is playing the game, such as scene change. By doing so, it is not required to compute the biological parameter while the user P is playing the game in real time, and therefore, it is possible to suppress the delay of progression of the game. As described above, according to this embodiment, because the game can be progressed smoothly, the user P can play the game without loosing the immersive feeling to the game.

In more detail, it is preferable that the biological parameter in this embodiment be a parameter that indicates the physical feature based on the life style of the user P. For example, the biological information of the user P indicates the physical feature such as, for example, the muscle mass and the body fat percentage and does not change moment by moment while the user P is playing the game. Therefore, there is no need for the game device 10 to acquire the biological information during the playing in real time. In other words, in the game device 10 in this embodiment, the biological information that undergoes changes over a long period of time is used as the feature of the user P. Thus, compared with a device using the biological information such as the pulse that changes moment by moment, the game device 10 has a high degree of freedom for the timing of acquiring the biological information of the user P. Thus, the game device 10 in this embodiment can compute the property parameter of the character on the basis of the biological information of the user P that is acquired at the timing that does not interfere with the progression of the game. The timing that does not interfere with the progression of the game in this context refers to, for example, an arbitrary timing before the property parameter is set, such as before the user P plays the game, during the standby time while the user P is playing the game, and so forth.

In other words, the biological information indicating the physical feature of the user P is the biological information related to the life style, and in addition, the biological information that undergoes changes over a long period of time may also be included. In this case, the control unit 100 can detect the biological information at the timing that does not interfere with the progression of the game and store it in the storage unit 130.

Meanwhile, in recent years, a gaming disorder is registered as a disease in WHO (World Health Organization) (see International Classification of Diseases 11th Revision). For the gaming disorder, it has been pointed out that an irregular life style is caused by playing the game for a long time. According to this embodiment, for the gaming disorder, the present invention can contribute to a treatment of the gaming disorder for the user P.

Specifically, in this embodiment, because the physical function of the user P is reflected to the physical function of the character in the game, the user P can grasp his/her own health status through the character. For example, when the physical function of the user P is lowered, the physical function of the character in the virtual space is also lowered. Therefore, the user P cannot achieve the movement of the character that is aimed by the user P, and thus, the user P recognizes that his/her own physical function or the health status has been lowered. Then, in order to improve the physical function of the character in the virtual space, the user P would attempt the improvement of the own physical function of the user P. As described above, the game device 10 in this embodiment provides the opportunity to the user P to improve the physical function. By doing so, the game device 10 facilitates the improvement in the life style that is achieved by the improvement in the motivation of the user P for exercise, and as a result, the game device 10 contributes to prevention of the gaming disorder and the treatment of the disease.

More specifically, the biological parameter in this embodiment is also a parameter indicating the health status of the user P. For example, as a state, in which the health status of the user P has been lowered, is improved to the normal state, it is preferred that there is a relationship in that the numerical value of the biological parameter approaches the standard value, and at the same time, the numerical value of the property parameter also approaches the standard value. When such a relationship is achieved, if the physical function of the user P is improved as the user P performs the exercise, etc., for example, the numerical value of the property parameter indicating the physical function of the character is also improved. Thus, compared to a state before the exercise, the user P can move the character in the virtual space in a sophisticated manner. As described above, as the motivation of the user P himself/herself for exercise is improved, the improvement in the life style of the user P, such as resolving of lack of exercise, etc., is facilitated.

In addition, as the game program 300 is executed, the control unit 100 in this embodiment computes the property parameter that determines the property of the character generated by the game program 300 in accordance with the biological parameter stored in the storage unit 130. As described above, the control unit 100 computes the biological parameter on the basis of the acquired biological information before the progression of the game and stores the biological parameter in the storage unit 130 in advance. Therefore, there is no need to computes the biological parameter during the user P is playing the game, and it is possible to suppress the delay of progression of the game.

In addition, the biological parameter stored in the storage unit 130 has a correlation with at least one of the physical function and the body shape of the user. Thus, the control unit 100 can reflect at least one of the physical function and the body shape based on the biological information indicating the physical feature of the user to the character.

In addition, the control unit 100 in this embodiment configures control means that controls the movement of the character displayed on the display device 20 in response to the control signal from the controller 12. Thus, it becomes easier for the user P to synchronize with the movement of the character in the virtual space, and the user P tends to have an affinity to the character. As a result, it is possible to achieve the technical object in that continuous interaction between a human and a machine is facilitated.

In addition, the game device 10 in this embodiment is provided with the bio-sensor (acquisition unit) 14 that has at least a single unit of a pair of electrodes (sensor) that converts the biological information of the user P into the numerical value. The biological parameter stored in the storage unit 130 is then computed on the basis of the biological information detected by using the bio-sensor 14.

As described above, with this embodiment, it is possible to measure the feature of the user P as the biological impedance by a pair of electrode portions provided on the bio-sensor 14. Therefore, the game device 10 can convert the biological information of the user P based on his/her own life style into the numerical value and reflect it to the physical function of the character in the virtual space. By doing so, the user P can obtain the immersive feeling to the game. In addition, the game device 10 can allow the user P to recognize his/her own health status through the character in the game and to have the opportunity to improve his/her own health status.

In addition, because the bio-sensor 14 is provided, even though the bothersome operational input by the user P is reduced when the property of the character is to be set, it is possible to suitably reflect the physical feature of the user P to the character. Therefore, it is possible to solve, at the same time, two conflicting issues: the improvement in the operational input-ability by the user P and the improvement in an accuracy in the reflection of the physical feature of the user P to the character.

In addition, the property parameter in this embodiment is associated with at least any one of the body height, the body weight, the circumference, the muscle mass, and the body fat percentage of the user P as the biological parameter.

With this embodiment, at least any one or at least two numerical values of the body height, the body weight, the circumference, the muscle mass, and the body fat percentage as the parameters clearly indicating the physical feature of the user P are reflected to the image of the character or the physical function of the character via the property parameter. As described above, because the physical function of the user P is reflected to the character, the user P can easily recognize his/her own physical function. Thus, the effect is afforded in that the game device 10 encourages the user P to improve the physical function.

In addition, in the game device 10 in this embodiment, in the virtual space realized by the game program 300, it is preferable that the body width as the property parameter indicating the presence/absence of the contact between the character and other object be at least associated with the circumference of the user P as the biological parameter.

As described above, the game device 10 in this embodiment determines the presence/absence of the contact between the character to which the circumference of the user P is reflected and the other object in the virtual space. By doing so, the user P can recognize the user P's own body shape by taking the contact between the character and the other object as the opportunity.

In other words, the game device 10 determines whether the body shape of the user P is good or bad, in other words, whether the user P is too fat or too thin, on the basis of the presence/absence of the contact between the character in the virtual space and the other object. Thus, in a case in which the character comes to contact with other object in the virtual space because the user P is too fat, the user P can have the opportunity to achieve an improvement to more healthy body shape, i.e., to make his/her own body shape to approach more skinny body shape. As described above, because the game device 10 includes a function of determining the body shape of the user P, the game device 10 can specifically contribute to a health enhancement of the user P.

In addition, in the game device 10 in this embodiment, in the virtual space realized by the game program 300, the attacking power (the property parameter) that indicates the level of the power applied to the other object by the character may be associated with at least one of the muscle mass and the body weight of the user P as the biological parameter.

With this embodiment, as the property of the character that is easily evoked from the muscle mass and the body weight of the user P, the attacking power can be set in accordance with the biological parameter. As described above, because the property parameter that is generally evoked is associated with the biological parameter, the immersive feeling of the user P to the game is increased further.

In addition, in this embodiment, the control unit 100 computes the property parameter by using the biological parameter and the arithmetic expression serving as the association information of the biological parameter and the property parameter, which are pre-set in the game program 300.

With this embodiment, the game device 10 can convert the biological parameter of the user P into the property parameter of the character unique to the game program 300 by using the unique arithmetic expression stored in the game program 300. By doing so, the game device 10 can reflect the feature of the user P to the characters unique to the various game programs 300.

In addition, it is preferable that the bio-sensor (the acquisition unit) 14 acquire at least one of an electrical resistance value, the body image data, the body temperature distribution data, and the elasticity index of skin of the user P.

As described above, by reflecting the detailed physical feature of the user P as the property of the character, it is possible to further increase the immersive feeling of the user P to the game. In addition, the biological information of the user P is a parameter related to the life style of the user P and is relatively unlikely to be changed in a short period of time. Therefore, the game device 10 can allow the storage unit 130 to store the biological parameter at the timing that does not interfere with the progression of the game.

In addition, it is preferable that the property parameter in this embodiment be a parameter that is associated with the biological parameter that features at least any one of the physical function and the external appearance of the user P.

The biological parameter in this embodiment may be converted into any property parameter that can be evoked from the biological parameter indicating at least any one feature of the physical function and the external appearance of the user P. As described above, it is possible to further increase similarity between the real physical function, etc. of the user P and the physical function of the character, etc. in the virtual space. Thus, it is possible to further improve the immersive feeling of the user P to the game.

In addition, the biological parameter in this embodiment includes a numerical value indicating the body composition of the user P.

With this embodiment, by using the numerical value of the body composition that is the biological information of the user P for the biological parameter, the physical function of the user P is directly reflected to the biological parameter. Thus, the property parameter computed on the basis of the biological parameter also reflects the physical function of the user P more clearly. Thus, the user P can obtain the immersive feeling to game. Furthermore, because the physical function of the user P is clearly reflected to the character, the user P can grasp his/her own health status through the character more accurately.

In addition, the body composition of the user P is the biological information related to the life style and is the biological information that undergoes the change over a long period of time relative to the biological information, such as the pulse, etc., that undergoes the change moment by moment. Thus, the game device 10 can acquire the biological information at the timing that does not interfere with the progression of the game and store it in the storage unit 130. The body composition is broadly classified to fat, muscle, bone, and water content. In addition, the biological parameter of the user P computed from these body compositions includes at least any one of the body weight, the muscle mass, a basal metabolic rate, an internal fat level, an estimated bone mass, and a body water content.

In addition, the program in this embodiment (steps S10 to step S14) is a program used for the computer provided with the storage unit 130 and the control unit 100 that executes the game program 300. The program causes the computer to execute: the acquisition step of acquiring the biological information indicating the physical feature of the user P; the biological parameter computing step of computing the biological parameter of the user P based on the biological information; the storing step of storing the biological parameter in the storage unit 130; and the property-parameter computing step of computing the property parameter that determines the property of the character generated by the game program 300 in accordance with the stored biological parameter. As described above, the functions of the respective units of the above-described control unit 100 may also be realized by the software.

Second Embodiment

Next, the game system 1 according to a second embodiment will be described. In the game system 1 in this embodiment, a part of the character generating processing is different from that in the first embodiment.

Specifically, the method of generating the character image 22 in step S13 of the above-described character generating processing is different from that in the first embodiment. In this embodiment, the property parameter generated in step S12 is used to generate the character image 22.

[Generation of Image of Character]

Figure 6:
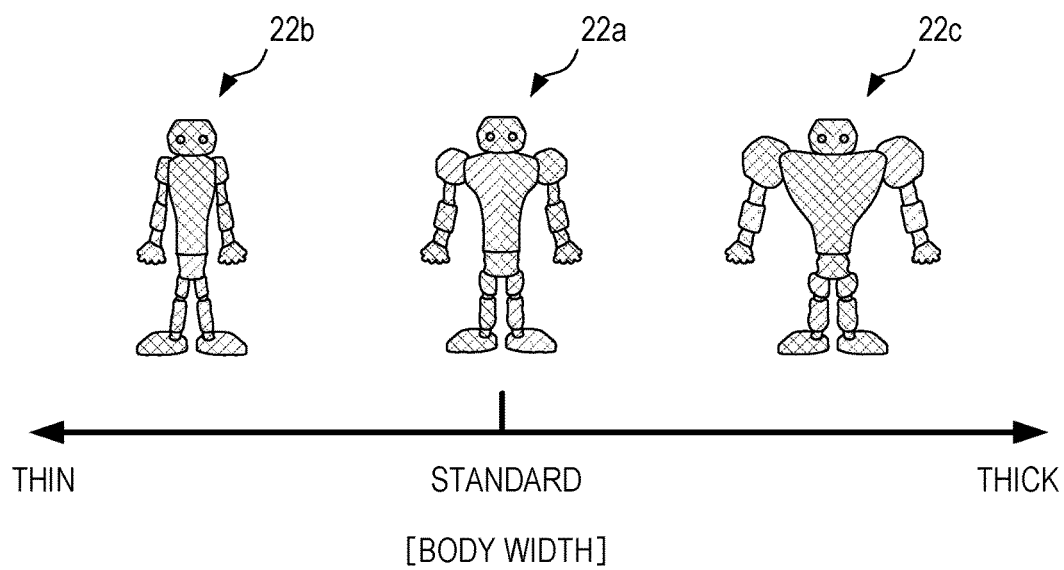
FIG. 6 is a diagram showing one example of an image generated by a character generating processing according to a second embodiment.

FIG. 6 is a diagram showing one example of the character image 22 generated by the character generating processing to which this embodiment is applied.

FIG. 6 shows the character image 22 that is changed in accordance with the value of the property parameter. As explained in the character generating processing described above, the body width of the character as the property parameter is at least associated with the circumference as the biological parameter of the user P.

In the above, for ease of understanding, the property parameter used for the generation of the character image 22 in this embodiment is the body width, and the body width is associated with the circumference of the user P as the biological parameter. Specifically, the circumference may be the abdominal circumference of the user P. The abdominal circumference of the user P has an advantage in that a bias due to the gender does not become large compared with the circumference of the chest part, for example.

As shown in FIG. 6, when the circumference of the user P is at the standard level, a character image 22a has the standard body width because the character image 22a is generated on the basis of the property parameter that is calculated in accordance with the standard circumference as the biological parameter.

When the circumference of the user P is smaller than the standard, in other words, when the user P has a thin body shape, a character image 22b has the body width that is smaller than the standard because the character image 22b is generated on the basis of the property parameter that is calculated in accordance with the circumference smaller than the standard as the biological parameter.

Furthermore, when the circumference of the user P is larger than the standard, in other words, when the user P has a fat body shape, a character image 22c has the body width that is larger than the standard because the character image 22c is generated on the basis of the property parameter that is calculated in accordance with the circumference larger than the standard as the biological parameter.

As described above, the property parameter in this embodiment is at least associated with the circumference of the user P as the biological parameter. In the example shown in FIG. 6, the width of a trunk of the character image 22 is defined in accordance with the circumference of the user P as a contour of the character image 22. The body width of the character image 22 is then changed in accordance with the circumference of the user P. The property parameter that indicates the contour of the character image 22 may be associated not only with the circumference or the body fat percentage as the biological parameter, but also with the body height. In this case, the body height of the user P is reflected to the character image 22.

With this embodiment, following operations and effects are afforded.

In the game device 10 in this embodiment, the character image (the image of character) 22 is generated on the basis of the property parameter.

As described above, with this embodiment, because the feature of the external appearance of the user P is reflected as the property of the character, the user P can recognize the change in his/her own external appearance through the game. For example, when the external appearance of the user P looks unhealthy, the character image 22 is also output to have the external appearance with unhealthy looking. By doing so, because the feature of the user P himself/herself is reflected to the external appearance of the character, the user P can the immersive feeling to the game. In addition, because the user P can visually recognize the change in the external appearance due to his/her own life style, if the life style is irregular, the user P can have the opportunity to improve the life style.

In addition, the property parameter in this embodiment is associated with at least one of the circumference and the body height of the user P as the biological parameter. The control unit 100 defines the contour of the image of the character on the basis of the property parameter that is associated with at least one of the circumference and the body height of the user P.

With this embodiment, the contour of the image of the character is associated with the circumference of the user P. Thus, by looking the character image 22 while playing the game, the user P can recognize his/her own body shape. When the body shape of the character is bad, for example, when the character image 22 has the fat body shape, the user P can have the opportunity to do the exercise for improving his/her own body shape to the standard shape. As a result, the user P can improve the health status and the life style by being encouraged by the game device 10 to do the exercise. In addition, the circumference of the user P is the biological information that undergoes the change over a long period of time relative to the biological information such as the pulse, etc., which undergoes the change in moment by moment on the basis of the life style, and the body height of the user P is the biological information that generally undergoes little change. Thus, it is possible to store the biological parameter in the storage unit 130 at the timing that does not interfere with the progression of the game.

Third Embodiment

Next, the game system 1 according to a third embodiment will be described. In the game system 1 in this embodiment, a part of the property-parameter generating processing is different from that in the first embodiment.

Figure 7:
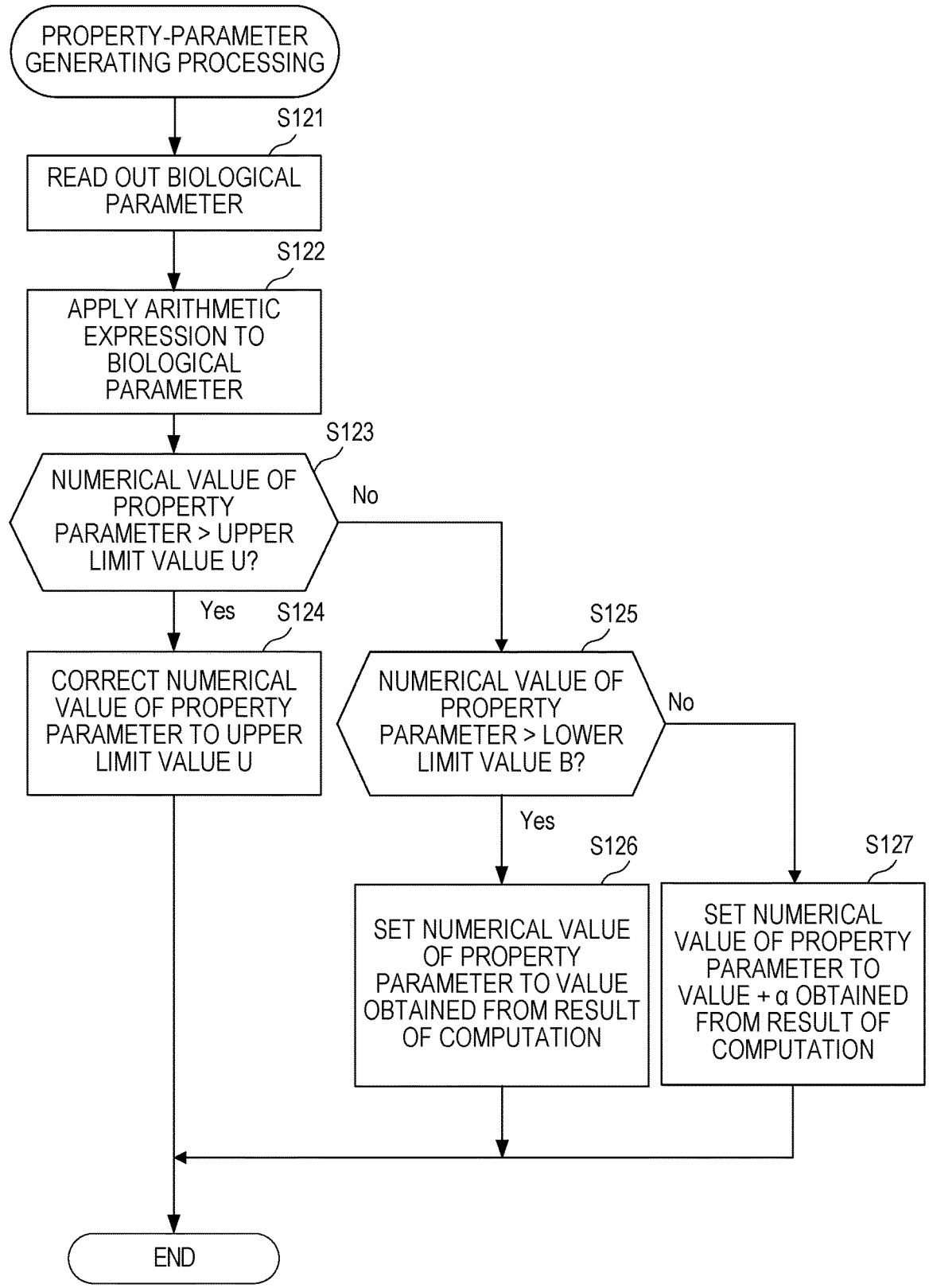
FIG. 7 is a flowchart showing one example of the property-parameter generating processing according to a third embodiment.

FIG. 7 is a flowchart showing one example of the property-parameter generating processing according to this embodiment. The same reference signs are given to processings that are the same as those in this embodiment, and description thereof will be omitted.

In this embodiment, a computing method of the property parameter in a case in which an upper limit value U and a lower limit value B are set for the numerical value of the property parameter will be described.

The control unit 100 computes the property parameter by executing the property-parameter generating processing shown in FIG. 7. As the property parameter is computed from the biological parameter in steps S121 to S122, the processing proceeds to step S123.

In step S123, the control unit 100 determines whether or not the numerical value of the property parameter is larger than the upper limit value U.

In step S123, when the control unit 100 determines that the numerical value of the property parameter is larger than the upper limit value U, the numerical value of the property parameter is determined as the upper limit value U in step S124, and the processing is terminated. In other words, the control unit 100 limits the maximum value of the numerical value in order to suppress excessive increase in the numerical value of the property parameter.

On the other hand, in step S123, when the control unit 100 determines that the numerical value of the property parameter is not larger than the upper limit value U, in other words, when the control unit 100 determines that the numerical value is smaller or equal to than the upper limit value U, in step S125, the control unit 100 determines whether or not the numerical value is larger than the lower limit value B.

In step S125, when the control unit 100 determines that the calculated numerical value of the property parameter is larger than the lower limit value B, the numerical value of the property parameter is determined as the numerical value in step S126, and the processing is terminated.

On the other hand, in step S125, when the control unit 100 determines that the calculated numerical value of the property parameter is not larger than the lower limit value B, in other words, when the control unit 100 determines that the numerical value is smaller or equal to than the lower limit value B, in step S127, the numerical value of the property parameter is determined as the numerical value obtained by adding a correction value a to the numerical value of the property parameter, and the processing is terminated. In other words, the control unit 100 limits the minimum value of the numerical value in order to suppress excessive decrease in the numerical value of the property parameter.

Figure 8:
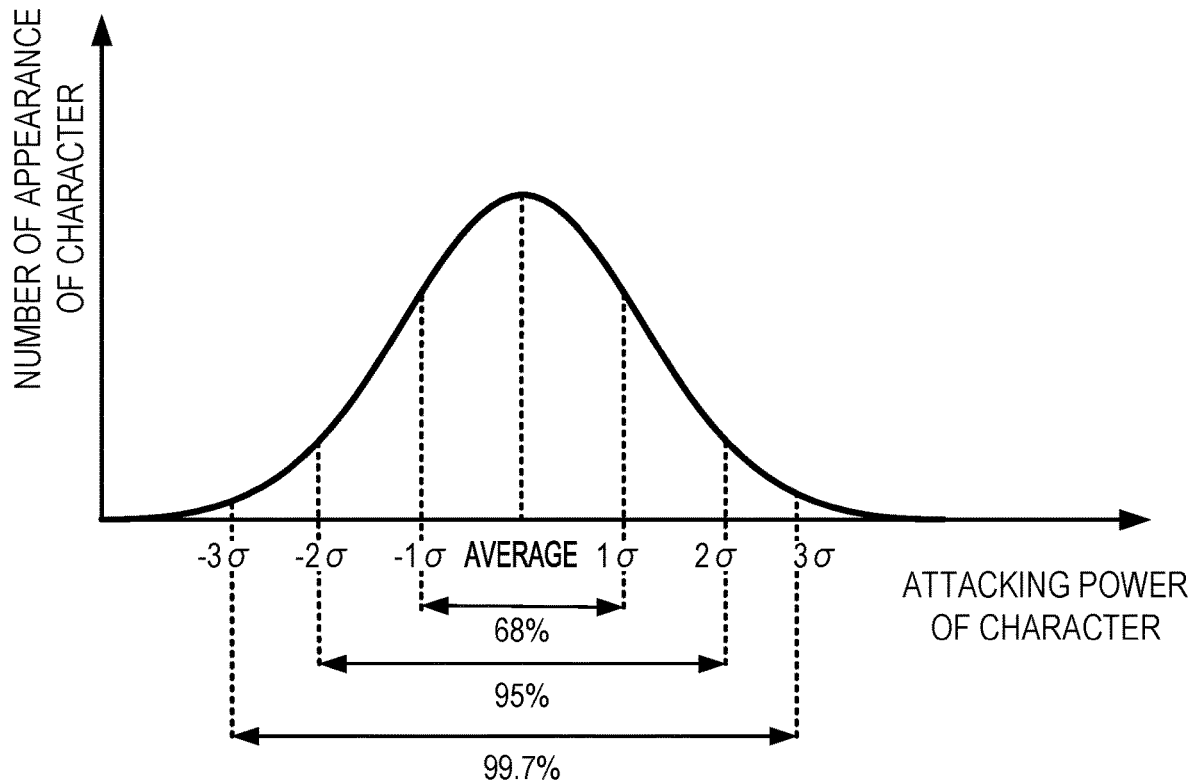
FIG. 8 is a conceptual diagram showing one example of a distribution of the parameters obtained by the property-parameter generating processing to which the present embodiment is applied.

FIG. 8 is a diagram showing a distribution of the numerical value of the biological parameter generated by the property-parameter generating processing in this embodiment. In FIG. 8, the horizontal axis shows the attacking power of the character among the property parameter, and the vertical axis shows a number of appearance of the character. As shown in FIG. 8, the results show that 95% of the numerical value of the biological parameter fall within a range of $2\sigma$ from the average, and substantially all of the numerical value of the biological parameter fall within a range of $3\sigma$.

With this embodiment, following operations and effects are afforded.

In the property-parameter generating processing in this embodiment, the game device 10 corrects the numerical value of the property parameter that is computed by using the biological parameter and limits the numerical value of the property parameter so as to fall within a predetermined range.

For example, in a case in which a numerical value of a muscular power of the user P is extremely large, the numerical value of the property parameter associated with the muscular power may also become extremely large. In this embodiment, because the computed value of the property parameter is corrected by setting the upper limit value U and the lower limit value B for such an extreme property parameter, it is possible to suppress the generation of the character having an extreme property.

By doing so, the game device 10 can suppress a phenomenon in which the property of the character to which the biological information of the user P is reflected becomes excessively advantageous or disadvantageous relative to other character. In addition, as described by using FIG. 8, the distribution, which is considered to be appropriate even in reality, is reproduced as the appearance rate of the character in the virtual space. Therefore, the user P can obtain a satisfying feeling for the game. Thus, it is possible to suppress the loss of the immersive feeling of the user P to the game.

Fourth Embodiment

Next, the game system 1 according to a fourth embodiment will be described.

In this embodiment, the body width, the attacking power, the jumping power, and a fire attacking power are set as the property parameters. In the following, the associating relationship between the property parameter and the biological parameter of the user P will be described.

[Types of Character]

Figure 9:
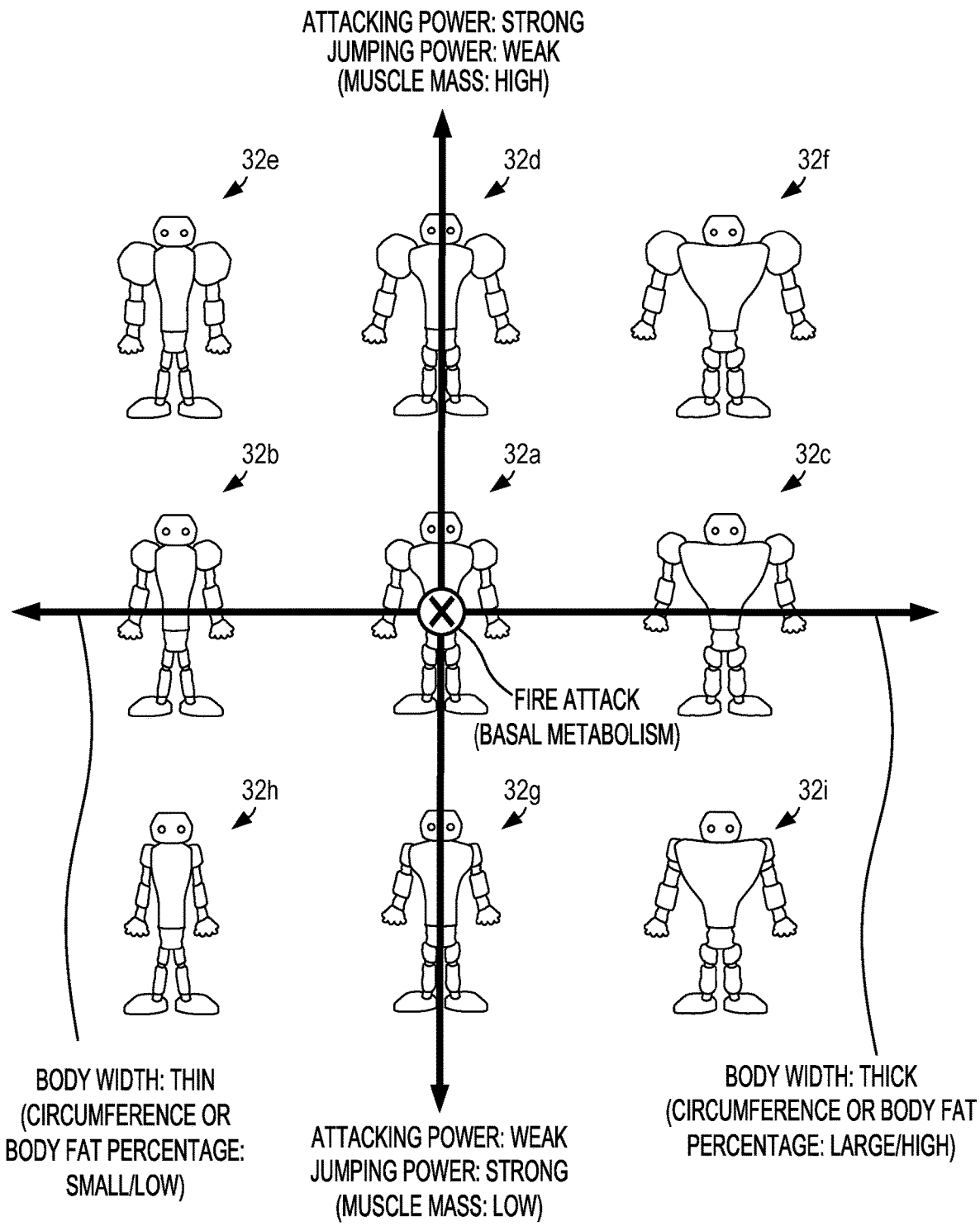
FIG. 9 is a diagram showing one example of a character generated by the character generating processing according to a fourth embodiment.

FIG. 9 is a diagram showing one example of the character generated by the character generating processing according to this embodiment. In this embodiment, FIG. 9 is a diagram showing nine types of characters that are generated in accordance with the biological parameter of the user P. In FIG. 9, the biological parameters are described within parentheses.

The horizontal axis in FIG. 9 shows a degree of the circumference or the body fat percentage as the biological parameter, and the vertical axis in FIG. 9 shows a degree of the muscle mass as the biological parameter. These nine types of the character is classified on the basis of determination result of the body shape that is determined from the muscle mass, and the circumference or the body fat percentage among the biological parameters of the user P. In this determination of the body shape, criteria of three stages are provided for the circumference or the body fat percentage, and in addition, criteria of three stages are provided for the muscle mass, and thereby, the determination is made which of the nine types of the body shape the body shape of the user P corresponds to.

In this embodiment, characters 32a to 32i are generated in accordance with the determination of the body shape. Specifically, when the body shape of the user P is determined as "the standard", the character 32a is generated as the corresponding property of the character. In addition, when the circumference or the body fat percentage and the muscle mass of the user P are smaller than or lower than the standard, the character 32h corresponding to this body shape is generated. In addition, when the circumference or the body fat percentage and the muscle mass of the user P is larger than or higher than the standard, the character 32f corresponding to this body shape is generated. As described above, the property of the character is determined in accordance with the results of the determination of the body shape of the user P.

As one example, as the muscle mass of the user P becomes lower than the standard, the attacking power as the property parameter is lowered, and at the same time, the jumping power is increased. In addition, as the muscle mass of the user P becomes higher than the standard, the attacking power as the property parameter is increased, and at the same time, the jumping power is lowered. The lower the circumference or the body fat percentage of the user P is, the thinner the body width becomes, and the higher the circumference or the body fat percentage of the user P is, the thicker the body width becomes. Here, the attacking power, the jumping power, and the body width as the property parameter are changed with the three stages.

The body width of the character may be calculated by using the above-described equation (1) or (2), the attacking power may be calculated by using the above-described equation (3) or (4), and the jumping power may be calculated by using the above-described equation (5) or (6). In addition, because the respective property parameters are changed stepwise as shown in FIG. 9, a numerical value that is obtained from the arithmetic expression such as the equations (1) to (6) and rounded to a predetermined unit may also be used as the property parameter.

In addition, the fire attacking power as the property parameter of the character is also determined. Here, the fire attacking power as the property parameter is associated with a basal metabolism as the biological parameter. For example, the fire attacking power of the character may be calculated by using the arithmetic expression such as following equation (7) or (8), similarly to the above-described equations (1) to (6).

$$\text{Fire Attacking Power of Character} = J \times \text{Basal Metabolism} + K \times \text{Body Fat Percentage} + L \quad (7)$$

$$\text{Fire Attacking Power of Character} = J1 \times \text{Basal Metabolism} + L1 \quad (8)$$

Respective coefficients J, J1, K, L, and L1 in the above-described equations (7) and (8) are set by taking the degree of contribution to and the normalization of the fire attacking power into consideration.

Alternatively, a numerical value that is obtained from the arithmetic expression such as the equation (7) or (8) and rounded to a predetermined unit may also be used as the fire attacking power such that the fire attacking power is changed in the three stages.

The fire attacking power of the character is changed along the axis extending in the vertical direction with respect to the plane of the drawing. In other words, although the fire attacking power is changed in accordance with the basal metabolism of the user P as the biological parameter, the external appearance of the character is not changed.

In the image generating unit 150, as the external appearance of the character, the images of the characters 32a to 32i are generated so as to respectively correspond to the above-described nine body shapes. In other words, the images of the character 32a to 32i are generated such that the actual body shape of the user P is reflected.

[Appearance Rate of Character]

Figure 10A:
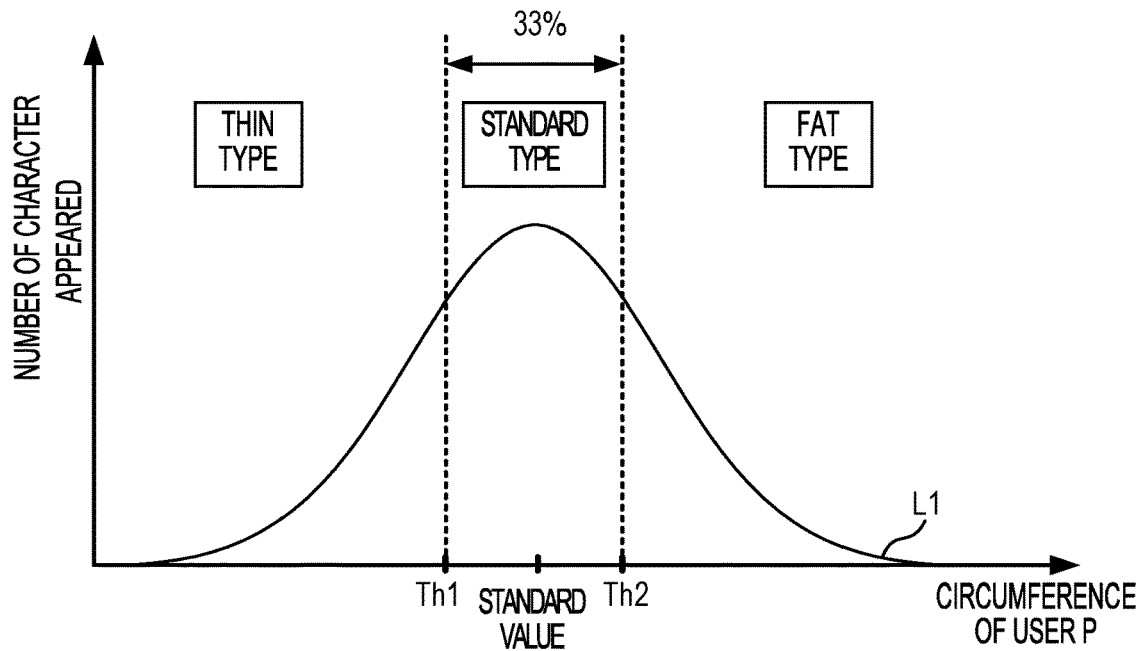
FIG. 10A is a diagram showing one example of an appearance rate of the character in the present embodiment.
Figure 10B:
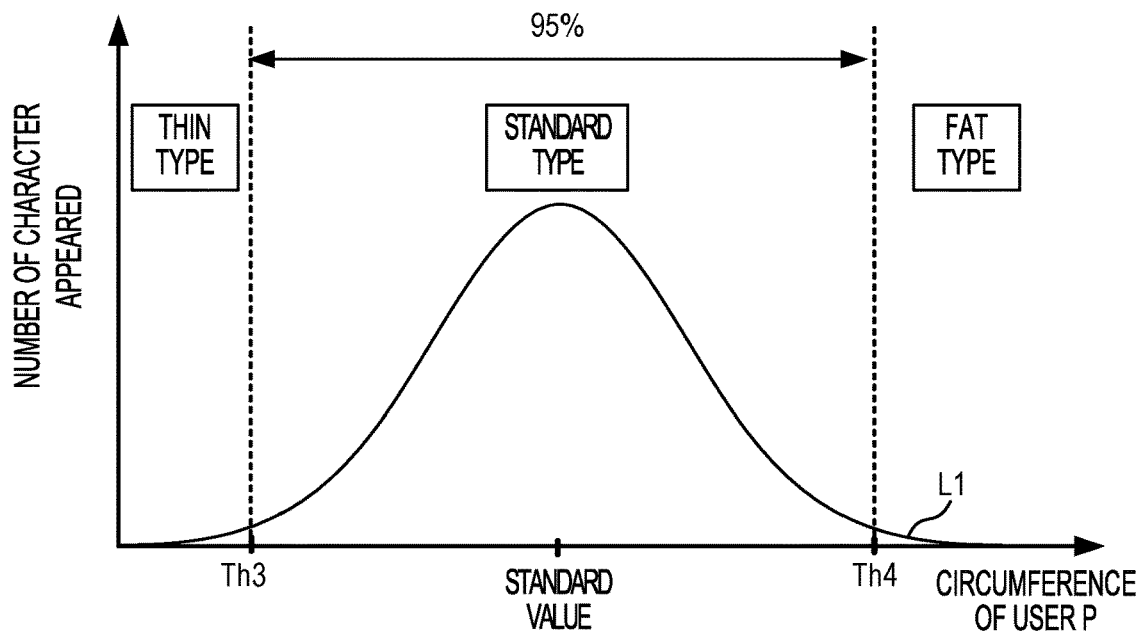
FIG. 10B is a diagram showing one example of the appearance rate of the character in the present embodiment.

Next, the appearance rate of the characters 32a to 32i of the above-described nine types will be described. FIGS. 10A and 10B show the appearance rate of the nine types of characters 32a to 32i in accordance with the circumferences as the biological parameters of a plurality of users P.

As described by using FIG. 9, the body width of the character is divided into the three stages. Here, for ease of understanding, the types of the body width of the character in the three stages will be described by calling them as a thin type, a standard type, and a fat type. Specifically, the characters classified as the thin type are the characters 32b, 32e, and 32h, the characters classified as the standard type are the characters 32a, 32d, and 32g, and the characters classified as the fat type are the characters 32c, 32f, and 32i.

In FIG. 10A, the appearance rate of the characters in the thin type, the standard type, and the fat type is shown. In other words, in a case in which the circumference as the biological parameter is smaller than a threshold value Th1, the appeared character is any of the character 32b, 32e, and 32h in the thin type. In addition, in a case in which the circumference is between the threshold value Th1 and Th2, the appeared character is any of the character 32a, 32d, and 32g in the standard type. In a case in which the circumference is larger than the threshold value Th2, the appeared character is any of the character 32c, 32f, and 32i in the fat type.

In addition, a distribution curve L1 shown in FIG. 10A is, for example, a curve that substantially matches with the distribution of the case in which a given number of Japanese people "N" (N is a natural number) is taken as a sample. In the example shown in FIG. 10A, the threshold values Th1 and Th2 are set such that a number of people having the circumference of the numerical value between the threshold value Th1 and the threshold value Th2 becomes about 33% of "N". In this case, the characters of the thin type, the standard type, and the fat type appear equally.

As described above, with the setting of the threshold values Th1 and Th2 shown in FIG. 10A, because the three types of characters will appear in an equal probability, the user P can have a substantially equal chance to operate the three types of characters. In addition, because the threshold values Th1 and Th2 are set to the values close to the standard value, in a case in which the body shape of the user P is changed slightly from the standard, there is a high possibility that the numerical value of the circumference is shifted beyond the threshold values Th1 and Th2. Therefore, the appeared character is changed in response to the slight change in the body shape of the user P, and therefore, the user P can visually recognize the slight change in his/her own body shape and can experience the functions that the character can exhibit in the virtual space.

On the other hand, the distribution curve L1 shown in FIG. 10B is also the curve that is the same as the distribution curve L1 shown in FIG. 10A.

In the example shown in FIG. 10B, the threshold values Th3 and Th4 are set such that a number of people falling within a range from a threshold value Th3 to a threshold value Th4 becomes about 95% of "N". Therefore, in the example shown in FIG. 10B, while the characters in the thin type and the fat type will appear scarcely, the character in the standard type will appear often.

With the example shown in FIG. 10B, because the threshold values Th3 and Th4 are the circumferences that the user P rarely has in general, the character in the thin type and the fat type do not appear. This is analogous to the tendency for the distribution for the real sample, in other words, the tendency in which the user P encounters a person of extremely thin type or fat type only at low probabilities in reality. Therefore, because even in the virtual space, the user P can experience the feeling similar to the real feeling, and therefore, it is possible to increase the immersive feeling of the user P to the game.

If the value of the biological parameter of the user P is applied to the determination of the body shape as is, a bias may be caused in the appearance rate of the characters 32a to 32i. In such a case, when the biological parameter is converted into the property parameter, the value of the property parameter may be adjusted in accordance with an attribute such as the gender, an age, an occupation, or the like of the character in the virtual space.

For example, when the gender of the user P is female, the user P generally has the circumference smaller than that of male, and thus, in accordance with the classification shown in FIG. 9, it is expected that the appearance rate of the characters 32b, 32e, and 32h with thin body width becomes high. In such a case, when the gender of the user P is female, it is preferable that the value of the property parameter be adjusted in accordance with the gender such that the appearance rate of the character of the specific type does not become excessively high. Alternatively, the threshold values Th1 to Th4 described above may be adjusted in accordance with the gender of the user P such that no bias is caused for the appearance rate of the character.

With this embodiment, following operations and effects are afforded.

In this embodiment, the game device 10 sets, for the biological parameter, the threshold values Th1 to Th4 for adjusting the appearance rate of the character. By doing so, the game device 10 determines the appearance rate of the character having the property parameter according to the threshold values Th1 to Th4.

As described in FIGS. 10A and 10B, by adjusting the threshold values Th1 to Th4, it is possible to increase the similarity between the reality and the virtual space, and so, it is possible to increase the immersive feeling of the user P to the game.

Fifth Embodiment

Figure 11:
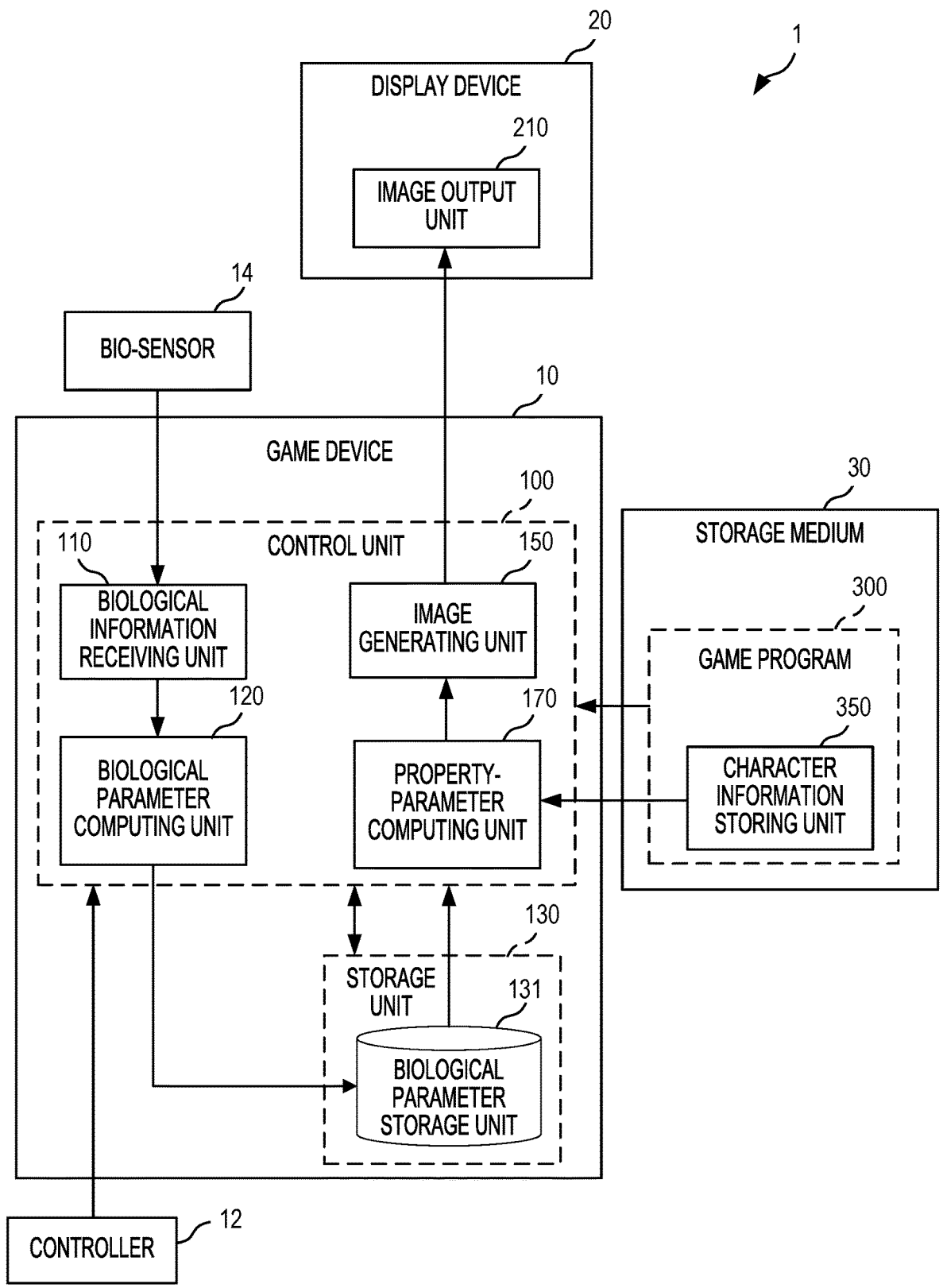
FIG. 11 is a diagram showing one example of the functional configuration according to the game device of a fifth embodiment.

Next, the game system 1 according to a fifth embodiment will be described. FIG. 11 is a diagram showing one example of the functional configuration of the game device 10 in this embodiment.

The game device 10 in this embodiment differs from that in the first embodiment in that a property-parameter computing unit 170 is provided. In addition, the storage medium 30 in this embodiment differs from that in the first embodiment in that a character information storing unit 350 is provided instead of the associated-information storing unit 310.

In the following, the configuration different from that of the first embodiment will be described. In addition, the same reference signs are given to the configuration same as that of the first embodiment, and description thereof will be omitted.

The property-parameter computing unit 170 receives information related to the type of the property parameter of the character from the character information storing unit 350 in response to the controlling signal from the control unit 100. In addition, the property-parameter computing unit 170 reads out the biological parameter from the biological parameter storage unit 131. The property-parameter computing unit 170 then performs computation to associate the biological parameter with the property parameter.

In addition, the property-parameter computing unit 170 in this embodiment determines the arithmetic expression for computing the associating relationship (the association information) between the biological parameter and the property parameter, in other words, the property parameter. The arithmetic expression in this embodiment may be stored in the storage unit 130 in advance.

The character information storing unit 350 stores the type of the property parameter for determining the property of the character that is generated by executing the game program 300. The type of the property parameter includes, as exemplified above, the body width, the attacking power, the jumping power, or the like.

In the character information storing unit 350, only the type of the property parameter for determining the property of the character is stored. In other words, in the character information storing unit 350, information that associates the biological parameter with the property parameter, for example, the arithmetic expression as described in the first embodiment is not stored.

In the game device 10 in this embodiment, the control unit 100 reads out the type of the property parameter from the character information storing unit 350 and sends the type of the property parameter to the property-parameter computing unit 170. The control unit 100 then computes the property parameter by applying the biological parameter read out from the biological parameter storage unit 131 to the arithmetic expression determined by the game device 10.

According to the above-described embodiment, following operations and effects are afforded.

In the game device 10 in this embodiment, the storage unit 130 stores the arithmetic expression (the association information) for the biological parameter and the property parameter. The control unit 100 computes the property parameter by using the biological parameter and the arithmetic expression.

With this embodiment, the game device 10 determines the relationship between the biological parameter and the property parameter and computes the property parameter on the basis of the associating relationship determined by the game device 10. Thus, there is no need to include the program that performs the association of the biological parameter and the property parameter in the game program 300 itself. Therefore, it is possible to make the game program 300 to have a simple configuration.

]Although the embodiments of the present invention have been described in the above, the respective embodiments described above merely illustrate a part of application examples of the present invention, and the technical scope of the present invention is not intended to be limited to the specific configurations of the above-described embodiments.

For example, in the above-described embodiment, the biological parameter is stored in the storage unit 130. However, not only the biological parameter, but also the biological information may also be stored in the storage unit 130. The information may also be stored in a server such as a cloud storage that can communicate with the game device 10. For example, the biological information of the user P in the past, the property parameter generated from the biological information, the image of the character, or the like may be stored in the cloud storage. In this case, the game device 10 may acquire the data from the cloud storage and apply it to the game device 10. By doing so, the character to which the feature of the user P in the past is reflected is generated.

In addition, the storage unit 130 may not be provided in the game device 10 and may be provided as a separate device. For example, the storage unit 130 may be included in an independent external storage medium such as an SSD (solid state drive), etc., or in the storage medium 30.

In addition, the cloud computer that can communicate with the game device 10 may be provided with the image generating unit 150. In this case, the cloud computer receives the biological information or the biological parameter stored in an electronic device such as a smartphone, etc. of the user P and computes the property parameter. The cloud computer then generates the character image 22 in the image generating unit 150, and the property parameter indicating the property of thus-generated character and the character image 22 may be sent to the game device 10.

In addition, the bio-sensor 14 in the above-described embodiment only has the function of converting the feature of the user P into the numerical value as the biological information. However, the bio-sensor 14 may also have a function of computing the biological parameter by converting the feature of the user P into the numerical value as the biological information.

Furthermore, in addition to the respective embodiment described above, the biological information that undergoes the change moment by moment may further be used as the biological parameter of the user P. For example, the game device 10 may estimate the correlation between the numerical value of the pulse and a degree of tension of a human on the basis of a theory in a bioengineering, etc., and may convert the degree of tension of the character as the property parameter into the numerical value from the pulse rate as the biological parameter. More specifically, the game device 10 may, for example, provide a tension level as the property parameter associated with the pulse rate of the user P for the character in the virtual space of an action-shooting game and may change a hit probability for the shooting in accordance with the tension level.

Furthermore, the association between the biological parameter and the property parameter in the above-described embodiment is not limited to those described above. For example, types of animals evoked from the biological parameter may be set in accordance with the biological parameter computed from the biological information. For example, when the numerical value of the pulse as the biological parameter of the user P is high, a small animal is generated as the character in the virtual space, and the external appearance and the physical function of the small animal as the character is determined by the property parameter associated with the biological parameter. Similarly, when the numerical value of the pulse of the user P is low, a large animal is generated as the character. As another example, when the body fat percentage as the biological parameter of the user P is high, a cattle or a sea lion may be generated as the character in the virtual space as evoked from the property parameter, and in the contrary, when the body fat percentage as the biological parameter of the user P is low, a leopard, a horse, or the like may be generated.

In other words, in the present invention, the property parameter indicating the property of the character and the biological parameter indicating the feature of the user P in the game program 300 may be in any associating relationship as long as the associating relationship can be evoked.

As another modification, a program that links a life rhythm in the virtual space of the character generated by using the above-described property parameter with the life rhythm of the user P in real life, such as a so-called a construction and management simulation game, a character training game, or the like, may be incorporated into the game program 300. By incorporating these games, a sleep state of the user P can be reflected to the sleep state of the character in the construction and management simulation game, an activity level of the user P can be reflected to the activity level of the character, or a content of a diet of the user P can be reflected to the content of the diet of the character. The sleep state, the activity level, and the content of the diet are converted into the numerical values by a sleep meter, the activity level meter, and an image sensor, respectively, and the property parameters are generated as the converted numerical values are sent to the game device 10 as the biological information. By doing so, the user P can reflect his/her own external appearance and physical function to the character in the virtual space, and at the same time, the user P can also reflect his/her own feature, such as the life rhythm, etc. to the character.

Especially, for a game that requires time commitment, where the longer the playing time is, the better the progression of the game becomes, an activity time of the user P other than the playing time, for example, a working hours and a mealtime of the user P interfere with the progression of the game. For the game that requires time commitment as described above, it is also possible to associate the life rhythm of the character in the virtual space with the life rhythm of the user P in the real life. As one example, it may be possible to perform the setting such that it is advantageous for the progression of the game if the user P carries out the working, the diet, or the like at the suitable life rhythm. By doing so, the user P can achieve the improve of the life style, such as correction of the irregular life rhythm, through the game.

The feature of the user P acquired as the biological information is not limited to body-related information as described above. For example, as the feature of the user P, the feature of the user P that can be converted into a numerical value by the bio-sensor 14 as the biological information, such as movement of eye of the user P, may also be used for the biological parameter. In addition, of course, the game device 10 need not be a dedicated device for executing the game program 300, and the game device 10 may be any electronic device as long as it is capable of receiving the biological information.

The present application claims a priority based on Japanese Patent Application No. 2019-231842 filed with the Japan Patent Office on Dec. 23, 2019. All the contents of this application are hereby incorporated by reference.

EXPLANATION OF REFERENCE 10 game device
100 control unit
130 storage unit
300 game program
P user

What is claimed is:

1. A game device comprising a memory and a processor configured to execute a game program, wherein the processor is configured to:
   acquire biological information indicating physical feature of a user operating the game device;
   compute a biological parameter of the user based on the biological information;
   store the biological parameter in the memory; and
   compute a property parameter in accordance with the biological parameter stored in the memory, the property parameter determining a property of a character generated by the game program,
   wherein the property parameter includes at least one of:
      a body width that is used when the character moves so as to pass through between other objects in a virtual space realized by the game program and is calculated based on a circumference of the user serving as the biological parameter,
      an attacking power that is calculated based on a muscle mass of the user serving as the biological parameter, and
      a jumping power that is calculated based on the muscle mass of the user serving as the biological parameter.

2. The game device according to claim 1, further comprising
   an acquisition unit having at least one sensor, the sensor being configured to detect the biological information, wherein
   the processor computes the biological parameter based on the biological information detected via the acquisition unit.

3. The game device according to claim 2, wherein
   the processor computes the property parameter so as to associate at least one of a body height, a body weight, the circumference, the muscle mass, and a body fat percentage of the user serving as the biological parameter.

4. The game device according to claim 3, wherein
   the processor generates an image of the character based on the property parameter.

5. The game device according to claim 4, wherein
   the processor computes the property parameter so as to associate at least one of the circumference and the body height of the user serving as the biological parameter, and
   the processor defines a contour of the image of the character based on the property parameter, the property parameter being associated with at least one of the circumference and the body height of the user.

6. The game device according to claim 1, wherein
   the processor associates the property parameter with at least the circumference of the user serving as the biological parameter, the property parameter indicating presence or absence of contact between the character and an other object in the virtual space realized by the game program.

7. The game device according to claim 2, wherein
   the processor associates the property parameter with at least the circumference of the user serving as the biological parameter, the property parameter indicating presence or absence of contact between the character and an other object in the virtual space realized by the game program.

8. The game device according to claim 3, wherein
   the processor associates the property parameter with at least the circumference of the user serving as the biological parameter, the property parameter indicating presence or absence of contact between the character and an other object in the virtual space realized by the game program.

9. The game device according to claim 4, wherein
   the processor associates the property parameter with at least the circumference of the user serving as the biological parameter, the property parameter indicating presence or absence of contact between the character and an other object in the virtual space realized by the game program.

10. The game device according to claim 5, wherein
    the processor associates the property parameter with at least the circumference of the user serving as the biological parameter, the property parameter indicating presence or absence of contact between the character and an other object in the virtual space realized by the game program.

11. The game device according to claim 3, wherein
    the processor associates the property parameter with at least one of the muscle mass and the body weight of the user serving as the biological parameter, the property parameter indicating a level of power acting on an other object by the character in the virtual space realized by the game program.

12. The game device according to claim 3, wherein
    the processor associates the property parameter with at least one of the muscle mass and the body weight of the user serving as the biological parameter, the property parameter indicating a level of power acting on an other object by the character in the virtual space realized by the game program.

13. The game device according to claim 3, wherein
    the processor associates the property parameter with at least one of the muscle mass and the body weight of the user serving as the biological parameter, the property parameter indicating a level of power acting on an other object by the character in the virtual space realized by the game program.

14. The game device according to claim 4, wherein
    the processor associates the property parameter with at least one of the muscle mass and the body weight of the user serving as the biological parameter, the property parameter indicating a level of power acting on an other object by the character in the virtual space realized by the game program.

15. The game device according to claim 5, wherein
    the processor associates the property parameter with at least one of the muscle mass and the body weight of the user serving as the biological parameter, the property parameter indicating a level of power acting on an other object by the character in the virtual space realized by the game program.

16. The game device according to claim 3, wherein
the processor associates the property parameter with at least one of the muscle mass and the body weight of the user serving as the biological parameter, the property parameter indicating a level of power acting on an other object by the character in the virtual space realized by the game program.

17. The game device according to claim 1, wherein
the memory stores association information between the biological parameter and the property parameter, and
the processor computes the property parameter by using the biological parameter and the association information.

18. The game device according to claim 1, wherein
the processor computes the property parameter by using the biological parameter and association information between the biological parameter and the property parameter, the association information being set in the game program in advance.

19. A non-transitory computer-readable recording medium in which a program is recorded, the program causing a computer, which is provided with a memory and a processor configured to execute a game program, to execute:

acquiring biological information indicating physical feature of a user;
computing a biological parameter of the user based on the biological information;
storing the biological parameter in the memory; and
computing, in accordance with the stored biological parameter, a property parameter determining a property of a character generated by the game program,
wherein the property parameter includes at least one of:
a body width that is used when the character moves so as to pass through between other objects in a virtual space realized by the game program and is calculated based on a circumference of the user serving as the biological parameter,
an attacking power that is calculated based on a muscle mass of the user serving as the biological parameter, and
a jumping power that is calculated based on the muscle mass of the user serving as the biological parameter.

20. The non-transitory computer-readable recording medium according to claim 19, wherein
the program further causes the computer to execute generating an image of the character based on the property parameter.

* * * * *